United States Patent
Subramaniam et al.

(10) Patent No.: US 11,291,646 B2
(45) Date of Patent: Apr. 5, 2022

(54) NOZZLE ASSEMBLY AND METHODS FOR USE

(71) Applicant: CRITITECH, INC., Lawrence, KS (US)

(72) Inventors: Bala Subramaniam, Lawrence, KS (US); Jahna Espinosa, Lawrence, KS (US); Gregory F. Johnson, Wichita, KS (US); Jacob M. Sittenauer, Lawrence, KS (US); Joseph S. Farthing, Lawrence, KS (US)

(73) Assignee: CritiTech, Inc., Lawrence, KS (US)

( * ) Notice: Subject to any disclaimer, the term of this patent is extended or adjusted under 35 U.S.C. 154(b) by 209 days.

(21) Appl. No.: 15/573,157

(22) PCT Filed: Jun. 6, 2016

(86) PCT No.: PCT/US2016/036012
§ 371 (c)(1),
(2) Date: Nov. 10, 2017

(87) PCT Pub. No.: WO2016/197100
PCT Pub. Date: Dec. 8, 2016

(65) Prior Publication Data
US 2018/0125783 A1    May 10, 2018

Related U.S. Application Data

(60) Provisional application No. 62/171,001, filed on Jun. 4, 2015, provisional application No. 62/171,060, filed
(Continued)

(51) Int. Cl.
*B01J 19/10*        (2006.01)
*A61K 31/337*     (2006.01)
(Continued)

(52) U.S. Cl.
CPC ............ *A61K 31/337* (2013.01); *A61J 3/02* (2013.01); *A61K 9/0019* (2013.01); *A61K 9/10* (2013.01);
(Continued)

(58) Field of Classification Search
CPC .... B01D 46/24; B01D 46/0068; B01D 11/00; B01J 3/02; B01J 3/008; B01J 19/10; A61J 3/02
(Continued)

(56) References Cited

U.S. PATENT DOCUMENTS 4,780,138 A * 10/1988 Bodine .................... C22B 3/22
                                                              422/127
5,480,540 A    1/1996 Day et al.
(Continued)

FOREIGN PATENT DOCUMENTS

CN    1129604 A    8/1996
CN    102319898 A    1/2012
(Continued)

OTHER PUBLICATIONS

Machine English translation of CN-102319898-B; Cao Xiaobao (Year: 2013).*
(Continued)

*Primary Examiner* — Francisco W Tschen
*Assistant Examiner* — Edgaredmanuel Troche
(74) *Attorney, Agent, or Firm* — McDonnell Boehnen Hulbert & Berghoff LLP (57) ABSTRACT

The present disclosure provides an apparatus and methods of use for isolating particles. An example apparatus includes (a) a vessel defining a pressurizable chamber, wherein the vessel includes a distal end and a proximal end, (b) an inlet of the pressurizable chamber at the proximal end of the vessel, (c) a nozzle positioned within the pressurizable
(Continued)

chamber, wherein the nozzle includes an inlet tube in fluid communication with the inlet of the pressurizable chamber, wherein the nozzle includes an outlet aperture, wherein the nozzle is adjustable to alter a distance between the proximal end of the vessel and the outlet aperture of the nozzle, and wherein the nozzle is adjustable to alter an angle between a longitudinal axis of the vessel and a longitudinal axis of the nozzle, and (d) an outlet of the pressurizable chamber at the distal end of the vessel.

22 Claims, 3 Drawing Sheets

Related U.S. Application Data on Jun. 4, 2015, provisional application No. 62/171,008, filed on Jun. 4, 2015.

(51) Int. Cl.

| | |
|---|---|
| A61K 9/00 | (2006.01) |
| A61K 9/10 | (2006.01) |
| A61K 9/14 | (2006.01) |
| A61K 9/16 | (2006.01) |
| B01J 19/26 | (2006.01) |
| B01J 2/04 | (2006.01) |
| B01J 3/00 | (2006.01) |
| B01J 4/00 | (2006.01) |
| A61K 9/51 | (2006.01) |
| A61J 3/02 | (2006.01) |
| B01D 46/24 | (2006.01) |
| B01J 3/02 | (2006.01) |
| B05B 1/34 | (2006.01) |
| B05B 13/02 | (2006.01) |

(52) U.S. Cl.
CPC .............. *A61K 9/14* (2013.01); *A61K 9/1605* (2013.01); *A61K 9/1682* (2013.01); *A61K 9/1688* (2013.01); *A61K 9/5192* (2013.01); *B01D 46/24* (2013.01); *B01J 2/04* (2013.01); *B01J 3/008* (2013.01); *B01J 3/02* (2013.01); *B01J 4/002* (2013.01); *B01J 19/10* (2013.01); *B01J 19/26* (2013.01); *B05B 1/3489* (2013.01); *B05B 13/0278* (2013.01); *B01D 2271/02* (2013.01); *B05D 2401/90* (2013.01)

(58) Field of Classification Search
USPC ....................................................... 264/5, 9
See application file for complete search history.

(56) References Cited

U.S. PATENT DOCUMENTS

| | | | | |
|---|---|---|---|---|
| 5,833,891 | A | * | 11/1998 | Subramaniam ...... A61K 9/1676 264/7 |
| 5,874,029 | A | | 2/1999 | Subramanian et al. |
| 6,113,795 | A | | 9/2000 | Subramanian et al. |
| 8,778,181 | B1 | * | 7/2014 | Johnson .................... A61J 3/02 210/260 |
| 9,586,923 | B2 | * | 3/2017 | Subramaniam ...... C07D 307/68 |
| 9,814,685 | B2 | * | 11/2017 | Baltezor ............... A61K 9/1605 |
| 10,076,880 | B2 | * | 9/2018 | Page ..................... B29C 48/465 |
| 2013/0161848 | A1 | * | 6/2013 | Gleeson ................... A61J 3/02 264/12 |
| 2015/0108671 | A1 | * | 4/2015 | Norikane ................... B01J 2/04 264/9 |
| 2015/0139865 | A1 | * | 5/2015 | Joseph ............... B01D 11/0203 422/281 |

FOREIGN PATENT DOCUMENTS

| | | | |
|---|---|---|---|
| CN | 102728414 A | | 10/2012 |
| CN | 102319898 B | * | 5/2013 |
| CN | 203847940 U | | 9/2014 |

OTHER PUBLICATIONS

The International Search Report (ISR) for PCT/US2016/036012 dated Aug. 25, 2016, pp. 1-3.
Written Opinion of the International Searching Authority for PCT/US2016/036012 dated Aug. 25, 2016, pp. 1-5.
Lee et al., "Supercritical antisolvent production of biodegradable micro- and nanoparticles for controlled delivery of paclitaxel", ScienceDirect, 125:96-106 (2008).

* cited by examiner

NOZZLE ASSEMBLY AND METHODS FOR USE

CROSS REFERENCE

This application is a U.S. national phase of International Application No. PCT/US2016/036012, filed on Jun. 6, 2016, which claims priority to U.S. Provisional Application No. 62/171,001, filed Jun. 4, 2015; U.S. Provisional Application No. 62/171,008, filed Jun. 4, 2015; and U.S. Provisional Application No. 62/171,060, filed Jun. 4, 2015, all of which are incorporated by reference herein in their entirety.

BACKGROUND

A need exists for apparatuses and methods capable of producing sub-micron and nano-sized particles. The need is particularly pronounced in the field of pharmaceutics. Conventional techniques for particle-size reduction currently practiced suffer from many disadvantages. As such, a need remains for improved equipment and processes for the preparation, harvesting and collection of small particles.

SUMMARY OF THE INVENTION

In one aspect, the invention comprises a nozzle assembly, including (a) a vessel defining a pressurizable chamber, wherein the vessel includes a distal end and a proximal end, (b) an inlet of the pressurizable chamber at the proximal end of the vessel, (c) a nozzle positioned within the pressurizable chamber, wherein the nozzle includes an inlet tube in fluid communication with the inlet of the pressurizable chamber, wherein the nozzle includes an outlet aperture, wherein the nozzle is adjustable to alter a distance between the proximal end of the vessel and the outlet aperture of the nozzle, and wherein the nozzle is adjustable to alter an angle between a longitudinal axis of the vessel and a longitudinal axis of the nozzle, and (d) an outlet of the pressurizable chamber at the distal end of the vessel.

In a second aspect, the invention includes a method for isolating particles comprising (a) providing a nozzle assembly including (i) a vessel defining a pressurizable chamber, wherein the vessel includes a distal end and a proximal end, (ii) a first inlet of the pressurizable chamber at the proximal end of the vessel, (iii) a nozzle positioned within the pressurizable chamber, wherein the nozzle includes an inlet tube in fluid communication with the first inlet of the pressurizable chamber, wherein the nozzle includes an outlet aperture, wherein the nozzle is adjustable to alter a distance between the proximal end of the vessel and the outlet aperture of the nozzle, and wherein the nozzle is adjustable to alter an angle between a longitudinal axis of the vessel and a longitudinal axis of the nozzle, and (iv) an outlet of the pressurizable chamber at the distal end of the vessel, (b) positioning a sonic energy source within the pressurizable chamber adjacent to the outlet aperture of the nozzle, (c) receiving a first fluid and a second fluid into the pressurizable chamber, wherein the first fluid is transported through the outlet aperture of the nozzle and onto the sonic energy source, and wherein the second fluid is transported through a second inlet of the pressurizable chamber to thereby create a plurality of particles within the pressurizable chamber, (d) receiving the plurality of particles through the outlet of the pressurizable chamber, (e) collecting the plurality of particles in a collection device, and (f) determining a size of one or more of the plurality of particles.

These as well as other aspects, advantages, and alternatives, will become apparent to those of ordinary skill in the art by reading the following detailed description, with reference where appropriate to the accompanying drawings.

DETAILED DESCRIPTION OF THE INVENTION

All references cited are herein incorporated by reference in their entirety. As used herein, the singular forms "a", "an" and "the" include plural referents unless the context clearly dictates otherwise. "And" as used herein is interchangeably used with "or" unless expressly stated otherwise. All embodiments of any aspect of the invention can be used in combination, unless the context clearly dictates otherwise.

As used herein, the term "solvent" refers to a fluid that dissolves a solute to form a solute-containing fluid (process fluid). The solvent must also be soluble in or miscible with an anti-solvent such that placing a solute-containing solvent into the anti-solvent will result in precipitation of the solute to form particles. The solvent is typically an organic solvent. Suitable organic solvents include ethanol, methanol, 1-propanol, isopropanol, 1-butanol, 2-butanol, tert-butanol, acetone, methylethylketone, dichloromethane, chloroform, hexafluoroisopropanol, diethyl ether, dimethylamide, and mixtures thereof.

As used herein, the term "anti-solvent" refers to a compressed fluid that is capable of forming a supercritical fluid under the conditions used. Suitable supercritical fluid-forming anti-solvents can comprise carbon dioxide, ethane, propane, butane, isobutane, nitrous oxide, xenon, sulfur hexafluoride and trifluoromethane.

As used herein, "longitudinal axis of the vessel" means an axis that intersects a top and bottom surface of the vessel.

As used herein, "longitudinal axis of the nozzle" means an axis that intersects a midpoint of the outlet aperture of the nozzle.

As used herein, the "specific surface area" is the total surface area of a particle per unit of particle mass as measured by the Brunauer-Emmett-Teller ("BET") isotherm (i.e.: the BET SSA).

As used herein, "about" means+/−5% of the recited value.

In one aspect, the present invention comprises a nozzle assembly, including (a) a vessel defining a pressurizable chamber, wherein the vessel includes a distal end and a proximal end, (b) an inlet of the pressurizable chamber at the proximal end of the vessel, (c) a nozzle positioned within the pressurizable chamber, wherein the nozzle includes an inlet tube in fluid communication with the inlet of the pressurizable chamber, wherein the nozzle includes an outlet aperture, wherein the nozzle is adjustable to alter a distance between the proximal end of the vessel and the outlet aperture of the nozzle, and wherein the nozzle is adjustable to alter an angle between a longitudinal axis of the vessel and a longitudinal axis of the nozzle, and (d) an outlet of the pressurizable chamber at the distal end of the vessel.

The systems and methods of the present invention provide a significant improvement over those disclosed in the prior art. The methods of the present invention are capable of producing the particles of the invention with significantly improved specific surface area (SSA) properties, and thus significantly improved therapeutic benefits. In particular, the inventors have unexpectedly been able to produce compositions comprising particles that have a mean specific surface area (SSA) of at least 18 $m^2/g$ an SSA using the novel nozzle assembly and methods of use as described herein. The increased specific surface area of the particles created by the nozzle assembly result in significant increases in dissolution rate compared to the raw particles and to milled products used for comparison. Dissolution takes place only at a solid/liquid interface. Therefore, increased specific surface area will increase the dissolution rate due to a larger number of molecules on the surface of the particle having contact with the dissolution media. This provides a significant improvement for use of such particles in, for example, tumor treatment.

The novel nozzle assembly and methods of use provide this significant improvement, at least in part, through use of the sonic energy source external to the nozzle and at a given distance from the outlet aperture of the nozzle to provide significantly enhanced sonic energy and enhanced disruption of the solvent-solute flow as it exits the nozzle. The prior art describes an exemplary process for particle production using compressed anti-solvent precipitation using converging-diverging nozzle to create sonic energy. In contrast, the methods of the present invention incorporate use of a sonic energy source external to the nozzle and just outside the orifice of the nozzle to provide significantly increased sonic energy and enhance disruption of the solvent/compound flow as it comes out of the nozzle, resulting in the production of particles with significantly enhanced SSA characteristics.

With reference to the Figures, as shown in FIG. 1A, the invention comprises a nozzle assembly 100 including a vessel 102 defining a pressurizable chamber 104. The vessel 102 includes a distal end 106 and a proximal end 108. The nozzle assembly 100 further includes an inlet 110 of the pressurizable chamber 104 at the proximal end 108 of the vessel 102. The nozzle assembly 100 further includes a nozzle 112 positioned within the pressurizable chamber 104. As shown in FIG. 1A, the nozzle 112 includes an inlet tube 114 in fluid communication with the inlet 110 of the pressurizable chamber 104. In addition, the nozzle 112 includes an outlet aperture 116. Further, as shown in FIG. 1A, the nozzle 112 is adjustable to alter a distance 118 between the proximal end 108 of the vessel 102 and the outlet aperture 116 of the nozzle 112. As shown in FIG. 1B, the nozzle 112 is further adjustable to alter an angle 120 between a longitudinal axis of the vessel 122 and a longitudinal axis of the nozzle 124. In addition, the nozzle assembly 100 includes an outlet 126 of the pressurizable chamber 104 at the distal end 106 of the vessel 102.

The nozzle assembly 100 may further include a first reservoir 128 and a second reservoir 130. The first reservoir 128 may include a supply of solvent, while the second reservoir 130 may include a supply of anti-solvent. The inlet 110 of the pressurizable chamber 104 may be in fluid communication with the first reservoir 128, and a second inlet 132 of the pressurizable chamber 104 may be in fluid communication with the second reservoir 130. In one example, the first reservoir 128 is in fluid communication with the inlet tube 114 of the nozzle 112, such that the solvent enters the pressurizable chamber 104 through the nozzle 112. Other examples are possible as well.

The outlet aperture 116 of the nozzle 112 may include a plurality of ridges to create a vortex within the nozzle 112 such that the solvent exits the nozzle 112 via turbulent flow. In another example, the nozzle 112 may include a porous frit interior to the nozzle 112 such that the solvent exits the nozzle 112 via turbulent flow. In yet another example, the outlet aperture 116 of the nozzle 112 may have a small diameter (as discussed in additional detail below) such that the solvent exits the nozzle 112 via turbulent flow. These various embodiments that cause turbulent flow may assist in mixing the solvent with the anti-solvent within the pressurizable chamber 104. Further, the inlet tube 114 of the nozzle 112 may have an inner diameter with a range from about 1.5875 mm to about 6.35 mm.

In other various embodiments, the outlet aperture 116 of the nozzle 112 has a diameter of between about 20 μm and about 125 μm, about 20 μm and about 115 μm, about 20 μm and about 100 μm, about 20 μm and about 90 μm, about 20 μm and about 80 μm, about 20 μm and about 70 μm, about 20 μm and about 60 μm, about 20 μm and about 50 μm, about 20 μm and about 40 μm, about 20 μm and about 30 μm, between about 30 μm and about 125 μm, about 30 μm and about 115 μm, about 30 μm and about 100 μm, about 30 μm and about 90 μm, about 30 μm and about 80 μm, about 30 μm and about 70 μm, about 30 μm and about 60 μm, about 30 μm and about 50 μm, about 30 μm and about 40 μm, between about 40 μm and about 125 μm, about 40 μm and about 115 μm, about 40 μm and about 100 μm, about 40 μm and about 90 μm, about 40 μm and about 80 μm, about 40 μm and about 70 μm, about 40 μm and about 60 μm, about 40 μm and about 50 μm, between about 50 μm and about 125 μm, about 50 μm and about 115 μm, about 50 μm and about 100 μm, about 50 μm and about 90 μm, about 50 μm and about 80 μm, about 50 μm and about 70 μm, about 50 μm and about 60 μm, between about 60 μm and about 125 μm, about 60 μm and about 115 μm, about 60 μm and about 100 μm, about 60 μm and about 90 μm, about 60 μm and about 80 μm, about 60 μm and about 70 μm, between about 70 μm and about 125 μm, about 70 μm and about 115 μm, about 70 μm and about 100 μm, about 70 μm and about 90 μm, about 70 μm and about 80 μm, between about 80 μm and about 125 μm, about 80 μm and about 115 μm, about 80 μm and about 100 μm, about 80 μm and about 90 μm, between about 90 μm and about 125 μm, about 90 μm and about 115 μm, about 90 μm and about 100 μm, between about 100 μm and about 125 μm, about 100 μm and about 115 μm, between about 115 μm and about 125 μm, about 20 μm, 30 μm, 40 μm, 50 μm, 60 μm, 70 μm, 80 μm, 90 μm, 100 μm, 115 μm, or about 120 μm. The nozzle 112 is inert to both the solvent and the compressed fluid used in the methods.

As described above and as shown in FIG. 1A, the nozzle 112 may be adjustable to alter a distance 118 between the proximal end 108 of the vessel 102 and the outlet aperture 116 of the nozzle 112. In addition, as shown in FIG. 1B, the nozzle 112 may be adjustable to alter an angle 120 between a longitudinal axis of the vessel 122 and a longitudinal axis of the nozzle 124. In one example, both the angle of the nozzle 112 and the vertical position of the nozzle 112 may be adjusted manually by a user. For example, the nozzle 112 may be positioned on a vertical support that can be adjusted to alter the distance 118 between the proximal end 108 of the vessel 102 and the outlet aperture 116 of the nozzle 112. Further, the nozzle 112 may be rotated manually to adjust the angle 120 between the longitudinal axis of the vessel 122 and the longitudinal axis of the nozzle 124.

In another example, the nozzle assembly 100 may include a motor coupled to the nozzle 112. In various examples, the motor may be configured to alter the distance 118 between the proximal end 108 of the vessel 102 and the outlet aperture 116 of the nozzle 112 and/or alter the angle 120 between the longitudinal axis of the vessel 122 and the longitudinal axis of the nozzle 124. Such a motor may be an electric motor powered by electrical power, or may be powered by a number of different energy sources, such as a gas-based fuel or solar power. The motor may be coupled directly or indirectly to the nozzle 112, such that when the motor is turned on the distance 118 between the proximal end 108 of the vessel 102 and the outlet aperture 116 of the nozzle 112 increases or decreases depending on the direction the motor rotates. The motor may be coupled to a series of gears that adjusts the distance 118 between the proximal end 108 of the vessel 102 and the outlet aperture 116 of the nozzle 112 and/or adjusts the angle 120 between the longitudinal axis of the vessel 122 and the longitudinal axis of the nozzle 124, or the motor may be coupled to a pulley system that adjusts the distance 118 between the proximal end 108 of the vessel 102 and the outlet aperture 116 of the nozzle 112 and/or adjusts the angle 120 between the longitudinal axis of the vessel 122 and the longitudinal axis of the nozzle 124. Other configurations are possible as well.

In another example, the nozzle 112 assembly may include an actuator coupled to the nozzle 112, where the actuator alters the distance 118 between the proximal end 108 of the vessel 120 and the outlet aperture 116 of the nozzle 112 and/or alters the angle 120 between the longitudinal axis of the vessel 122 and the longitudinal axis of the nozzle 124. Such an actuator may be an electro-mechanical actuator, including an electric motor that converts a rotary motion of the electric motor to a linear displacement via a linkage system. Other potential actuators are possible as well, such as hydraulic actuators, pneumatic actuators, piezoelectric actuators, linear motors, or telescoping linear actuators, as examples.

In further examples, the nozzle assembly 100 may include a plurality of nozzles, with each nozzle positioned at a different angle between a longitudinal axis of the vessel and a longitudinal axis of the nozzle and/or a different distance between the nozzle orifice and the sonic energy source. A given nozzle of the plurality of nozzles may be chosen for a given production run to produce a certain type of particle having a given SSA. Other example embodiments are possible as well.

Figure 1A:
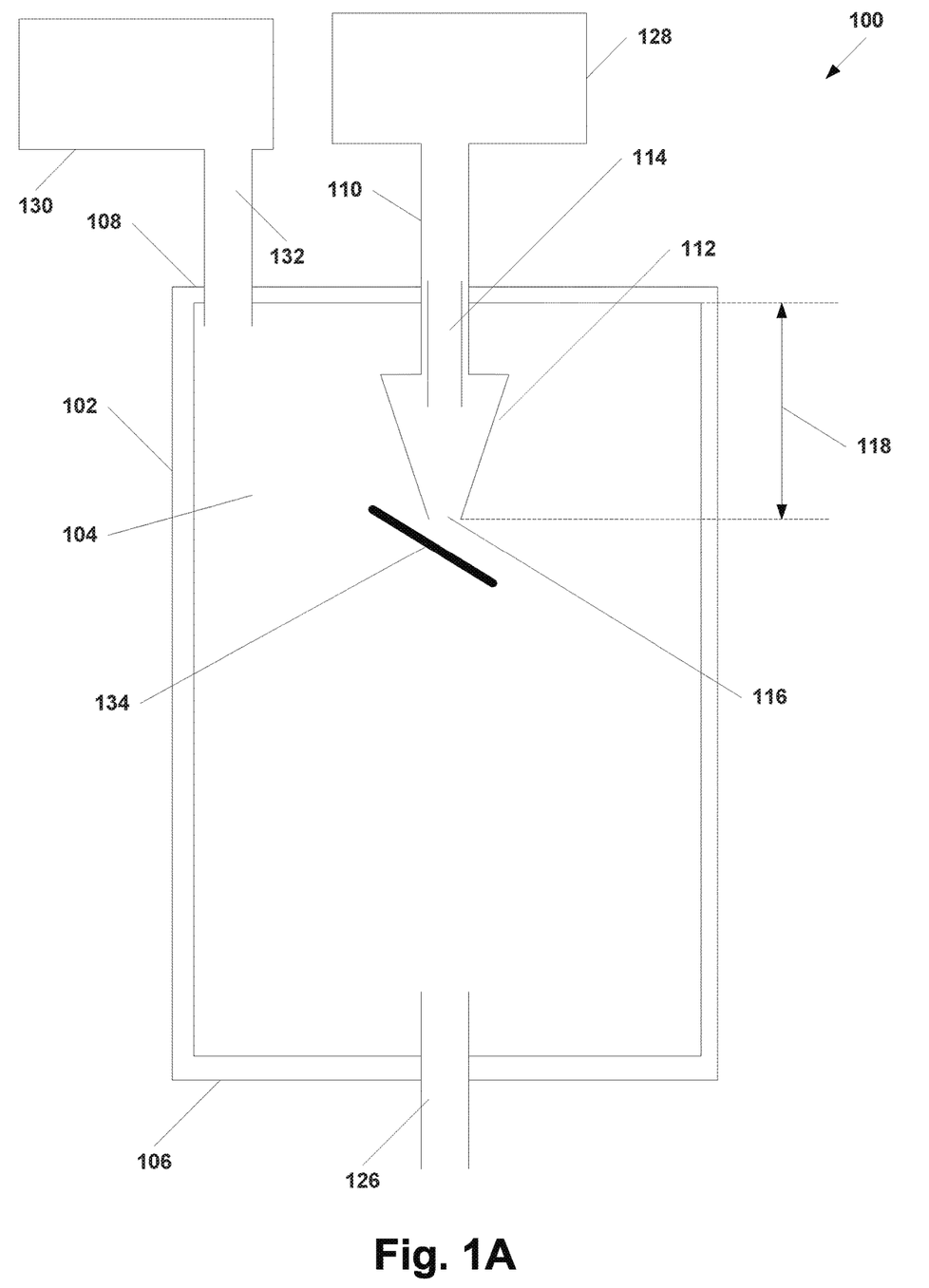
FIG. 1A illustrates a cross-section view of an example nozzle assembly, according to an example embodiment.
Figure 1B:
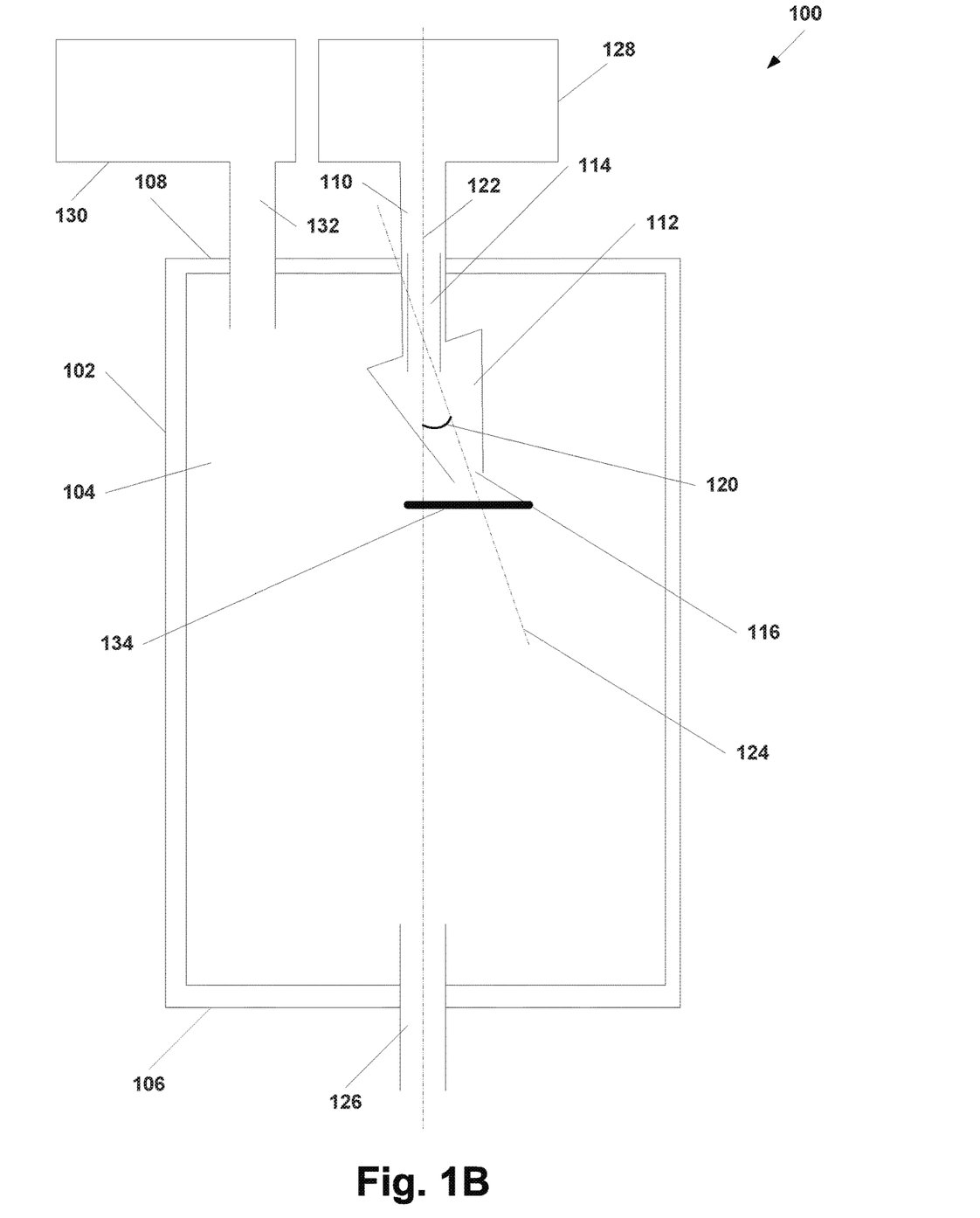
FIG. 1B illustrates a cross-section view of another example nozzle assembly, according to an example embodiment.

In one example, as shown in FIGS. 1A and 1B, the nozzle assembly further includes a sonic energy source 134 positioned adjacent to the outlet aperture 116 of the nozzle 112. In one example, the sonic energy source 134 may include a sonic probe extending within the pressurizable chamber 104. In another example, the sonic energy source 134 may include a sonic surface positioned in the pressurizable chamber 104. The sonic waves from the sonic energy source 134 cause the liquids in the pressurizable chamber 104 to shatter, thereby enhancing mixing of the solvent and anti-solvent solutions to create particles within the pressurizable chamber 104. In one example, the sonic energy source 134 is positioned at an angle of 45 degrees with respect to the longitudinal axis of the nozzle 124. Other angles are possible as well. In one example, the sonic energy source 134 may be adjustable to alter a distance between the outlet aperture 116 of the nozzle 112 and the sonic energy source 134. Further, the sonic energy source 134 may be adjustable to alter an angle between the sonic energy source 134 and the longitudinal axis of the nozzle 124.

In various embodiments, the outlet aperture 116 of the nozzle 112 is located between about 2 mm and about 20 mm, about 2 mm and about 18 mm, about 2 mm and about 16 mm, about 2 mm and about 14 mm, about 2 mm and about 12 mm, about 2 mm and about 10 mm, about 2 mm and about 8 mm, about 2 mm and about 6 mm, about 2 mm and about 4 mm, about 4 mm and about 20 mm, about 4 mm and about 18 mm, about 4 mm and about 16 mm, about 4 mm and about 14 mm, about 4 mm and about 12 mm, about 4 mm and about 10 mm, about 4 mm and about 8 mm, about 4 mm and about 6 mm, about 6 mm and about 20 mm, about 6 mm and about 18 mm, about 6 mm and about 16 mm, about 6 mm and about 14 mm, about 6 mm and about 12 mm, about 6 mm and about 10 mm, about 6 mm and about 8 mm, about 8 mm and about 20 mm, about 8 mm and about 18 mm, about 8 mm and about 16 mm, about 8 mm and about 14 mm, about 8 mm and about 12 mm, about 8 mm and about 10 mm, about 10 mm and about 20 mm, about 10 mm and about 18 mm, about 10 mm and about 16 mm, about 10 mm and about 14 mm, about 10 mm and about 12 mm, about 12 mm and about 20 mm, about 12 mm and about 18 mm, about 12 mm and about 16 mm, about 12 mm and about 14 mm, about 14 mm and about 20 mm, about 14 mm and about 18 mm, about 14 mm and about 16 mm, about 16 mm and about 20 mm, about 16 mm and about 18 mm, and about 18 mm and about 20 mm, from the sonic energy source 134.

In various further embodiments, the sonic energy source 134 produces sonic energy with an amplitude between about 1% and about 100% of the total power that can be generated using the sonic energy source. In light of the teachings herein, one of skill in the art can determine an appropriate sonic energy source having a specific total power output to be used. In one embodiment, the sonic energy source has a total power output of between about 500 and about 900 watts; in various further embodiments, between about 600 and about 800 watts, about 650-750 watts, or about 700 watts.

In various further embodiments, the sonic energy source produces sonic energy with a power output between about 5% and about 100%, about 10% and about 100%, 20% and about 100%, about 30% and about 100%, about 40% and about 100%, about 50% and about 10%, about 60% and about 100%, about 70% and about 100%, about 80% and about 100%, about 90% and about 100%, about 1% and about 90%, about 5% and about 90%, about 10% and about 90%, about 20% and about 90%, about 30% and about 90%, about 40% and about 90%, about 50% and about 90%, about 60% and about 90%, about 70% and about 90%, about 80% and about 90%, about 1% and about 80%, about 5% and about 80%, about 10% and about 80%, about 20% and about 80%, about 30% and about 80%, about 40% and about 80%, about 50% and about 80%, about 60% and about 80%, about 70% and about 80%, about 1% and about 70%, about 5% and about 70%, about 10% and about 70%, about 20% and about 70%, about 30% and about 70%, about 40% and about 70%, about 50% and about 70%, about 60% and about 70%, about 1% and about 60%, about 5% and about 60%, about 10% and about 60%, about 20% and about 60%, about 30% and about 60%, about 40% and about 60%, about 50% and about 60%, about 1% and about 50%, about 5% and about 50%, about 10% and about 50%, about 20% and about 50%, about 30% and about 50%, about 40% and about 50%, about 1% and about 40%, about 5% and about 40%, about 10% and about 40%, about 20% and about 40%, about 30% and about 40%, about 1% and about 30%, about 5% and about 30%, about 10% and about 30%, about 20% and about 30%, about 1% and about 20%, about 5% and about 20%, about 10% and about 20%, about 1%, 5%, 10%, 20%, 30%, 40%, 50%, 60%, 70%, 80%, 90%, or about 100% of the total power that can be generated using the sonic energy source. In various embodiments, the sonic energy source produces sonic energy with power output of about 1%-80%, 20-80%, 30-70%, 40-60%, or about 60% of the total power that can be generated using the sonic energy source.

In light of the teachings herein, one of skill in the art can determine an appropriate frequency to be utilized on the sonic energy source. In one embodiment, a frequency of between about 18 and about 22 kHz on the sonic energy source is utilized. In various other embodiments, a frequency of between about 19 and about 21 kHz, about 19.5 and about 20.5, or, a frequency of about 20 kHz on the sonic energy source is utilized. Any suitable source of sonic energy may be used that is compatible with the methods of the invention, including but not limited to sonic horn, a sonic probe, or a sonic plate.

Further still, the components of the nozzle assembly 100 may be a part of a larger particle production system. Such a particle production system may include one or more nozzle assemblies such as those described above, a sonic energy source positioned adjacent to the orifice of each nozzle, one or more particle filtration systems in communication with one or more nozzle assemblies, and one or more particle collection devices in communication with the one or more particle filtration systems. In one example, the one or more particle filtration systems comprise a tandem particle filtration system including at least one high pressure harvesting filter system and at least one low pressure collection filter system in tandem and downstream to the harvesting filter. In such an example, the particle production system may include at least two particle harvesting filters, two particle collection filters and two collection devices.

In one example, the particle collection devices in such particle production systems may include a collection vessel defining a chamber, wherein the collection vessel includes a distal end and a proximal end, an inlet port extending from the proximal end of the collection vessel, wherein the inlet port is in fluid communication with the chamber, and an outlet port extending from the proximal end of the collection vessel, and wherein the outlet port includes a porous material positioned between the chamber and the outlet port. The collection device may further include a sampling tube having a distal end and a proximal end, wherein the proximal end of the sampling tube extends from the proximal end of the collection vessel, and wherein the distal end of the sampling tube extends into the chamber. The sampling tube may be configured to remove a small sample of particles from the chamber during a particle production run in which additional particles are being formed. The sampling tube may include a sample thief that enables an operator to remove a small sample of particles without opening the chamber or removing the sampling tube from the rest of the collection device during processing. This enables an operator to test a small sample of particles to ensure that the product is within specifications as the process continues to run. For example, particle size or residual solvent analysis may be performed on the sample. If the measured specifications do not match the desired specifications, the particle formation process may be tweaked to correct the situation before an entire batch of product is created. In such an example, the outlet 126 of the nozzle assembly 100 may be coupled to the inlet port of the collection device.

In another example, the particle production system comprises at least one of a) two particle harvesting filters, two particle collection filters and two collection devices; b) two particle harvesting filters, one particle collection filter and one or more collection devices; c) two particle harvesting filters, two particle collection filters and one or more collection devices; d) two particle harvesting filters, one particle collection filter and one or more collection devices; e) two tandem filter particle harvesting and collection devices arranged in parallel: f) two or more particle harvesting filters arranged in parallel, one particle collection filter and two or more collection devices arranged in parallel; g) two or more precipitation chambers; h) at least two tandem filter particle filtration systems; i) at least two collection devices; or j) a combination thereof.

In another aspect, the invention provides methods for isolating particles comprising (a) providing a nozzle assembly including (i) a vessel defining a pressurizable chamber, wherein the vessel includes a distal end and a proximal end, (ii) a first inlet of the pressurizable chamber at the proximal end of the vessel, (iii) a nozzle positioned within the pressurizable chamber, wherein the nozzle includes an inlet tube in fluid communication with the first inlet of the pressurizable chamber, wherein the nozzle includes an outlet aperture, wherein the nozzle is adjustable to alter a distance between the proximal end of the vessel and the outlet aperture of the nozzle, and wherein the nozzle is adjustable to alter an angle between a longitudinal axis of the vessel and a longitudinal axis of the nozzle, and (iv) an outlet of the pressurizable chamber at the distal end of the vessel, (b) positioning a sonic energy source within the pressurizable chamber adjacent to the outlet aperture of the nozzle, (c) receiving a first fluid and a second fluid into the pressurizable chamber, wherein the first fluid is transported through the outlet aperture of the nozzle and onto the sonic energy source, and wherein the second fluid is transported through a second inlet of the pressurizable chamber to thereby create a plurality of particles within the pressurizable chamber, (d) receiving the plurality of particles through the outlet of the pressurizable chamber, (e) collecting the plurality of particles in a collection device, and (f) determining a size of one or more of the plurality of particles, wherein steps (c), (d), and (e) are carried out under supercritical temperature and pressure for the first and second fluids.

The methods of the invention involve contacting a solution, including a solvent with at least one compound of interest (including but not limited to an active pharmaceutical ingredient) dispersed in the solvent, with a compressed fluid at supercritical conditions for the compressed fluid, so as to cause the compressed fluid to deplete the solvent and precipitate the compound away as extremely small particles. In particular, the supercritical conditions are at or above 31.1 C and 1071 psi. In one example, the temperature may range from about 31.1° C. to about 60° C., and the pressure may range from about 1071 psi to about 1800 psi.

The methods of the present invention provide a significant improvement over methods such as those disclosed in U.S. Pat. Nos. 5,833,891; 5,874,029; 6,113,795; and 8,778,181 (incorporated herein by reference in their entirety) using a compressed fluid in combination with appropriate solvents to reproducibly precipitate compounds as fine particles that have a narrow size distribution. The methods of the present invention are capable of producing the particles of the invention with significantly improved SSA and dissolution properties, and thus significantly improved therapeutic benefits. The methods provide this significant improvement, at least in part, through use of the sonic energy source external to the nozzle and at the recited distance from the nozzle orifice to provide significantly enhanced sonic energy and enhanced disruption of the solvent-solute flow as it exits the nozzle compared to the methods disclosed U.S. Pat. Nos. 5,833,891 and 5,874,029 that use a converging-diverging nozzle to create the sonic energy.

Figure 2:
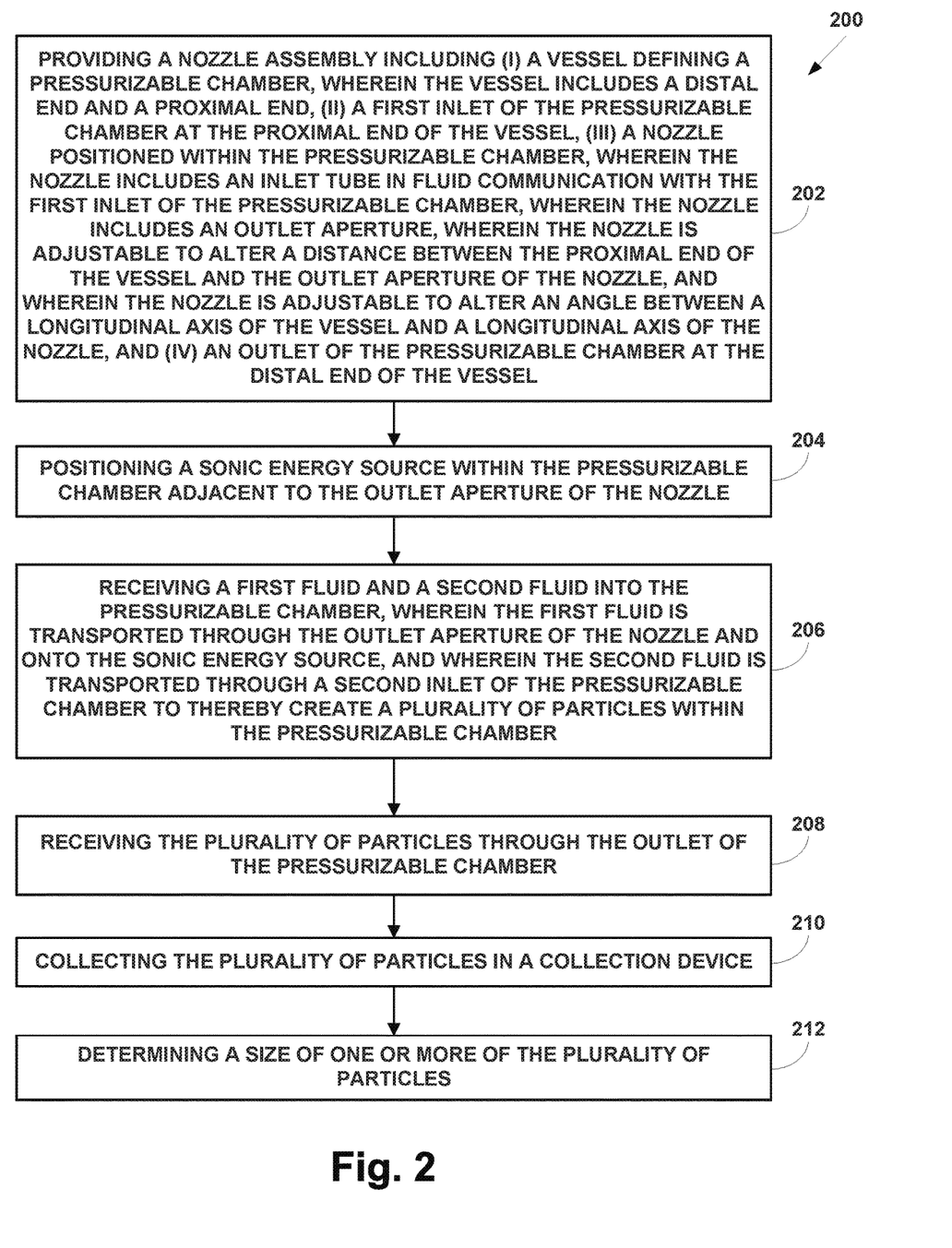
FIG. 2 is a block diagram of a method, according to an example embodiment.

FIG. 2 is a block diagram of a method 200, according to an example embodiment. Method 200 shown in FIG. 2 presents an embodiment of a method that could be used with the nozzle assembly 100, for example. Method 200 may include one or more operations, functions, or actions as illustrated by one or more of blocks 202-212. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 200 and other processes and methods disclosed herein, the flowchart shows functionality and operation of one possible implementation of present embodiments. In this regard, each block may represent a module, a segment, a portion of a manufacturing or operation process, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

In addition, for the method 200 and other processes and methods disclosed herein, each block in FIG. 2 may represent circuitry that is wired to perform the specific logical functions in the process.

At block 202, the method 200 includes providing a nozzle assembly including (i) a vessel defining a pressurizable chamber, wherein the vessel includes a distal end and a proximal end, (ii) an inlet of the pressurizable chamber at the proximal end of the vessel, (iii) a nozzle positioned within the pressurizable chamber, wherein the nozzle includes an inlet tube in fluid communication with the inlet of the pressurizable chamber, wherein the nozzle includes an outlet aperture, wherein the nozzle is adjustable to alter a distance between the proximal end of the vessel and the outlet aperture of the nozzle, and wherein the nozzle is adjustable to alter an angle between a longitudinal axis of the vessel and a longitudinal axis of the nozzle, and (iv) an outlet of the pressurizable chamber at the distal end of the vessel. Any suitable pressurizable chamber may be used, including but not limited to those disclosed in U.S. Pat. Nos. 5,833,891 and 5,874,029.

At block 204, the method 200 includes positioning a sonic energy source within the pressurizable chamber adjacent to the outlet aperture of the nozzle. At block 206, the method 200 includes receiving a first fluid and a second fluid into the pressurizable chamber, wherein the first fluid is transported through the outlet aperture of the nozzle and onto the sonic energy source, and wherein the second fluid is transported through a second inlet of the pressurizable chamber to thereby create a plurality of particles within the pressurizable chamber. In one example, the first fluid comprises a solution comprising at least one solvent and at least one solute comprising a compound of interest, and the second fluid comprises a compressed fluid under supercritical temperature and pressure. Any suitable solvent and solute may be used; exemplary such solutes and solvents are disclosed in U.S. Pat. Nos. 5,833,891 and 5,874,029. In various other non-limiting embodiments, the solvent may comprise acetone, ethanol, methanol, dichloromethane, ethyl acetate, chloroform, acetonitrile, and suitable combinations thereof. In one embodiment, the solute/compound is paclitaxel and the solvent is acetone. In another embodiment, the solute/compound is docetaxel and the solvent is acetone. The solvents should comprise at least about 80%, 85%, or 90% by weight of the overall solution. The compressed fluid is capable of forming a supercritical fluid under the conditions used, and the solute that forms the particles is poorly soluble or insoluble in the compressed fluid. As is known to those of skill in the art, a supercritical fluid is any substance at a temperature and pressure above its critical point, where distinct liquid and gas phases do not exist. Steps (c), (d), and (e), of the methods of the invention are carried out under supercritical temperature and pressure for the compressed fluid, such that the compressed fluid is present as a supercritical fluid during these processing steps.

The compressed fluid can serve as an anti-solvent and can be used to remove unwanted components in the particles. Any suitable compressed fluid may be used in the methods of the invention; exemplary such compressed fluids are disclosed in U.S. Pat. Nos. 5,833,891 and 5,874,029. In one non-limiting embodiment, suitable supercritical fluid-forming compressed fluids can comprise carbon dioxide, ethane, propane, butane, isobutane, nitrous oxide, xenon, sulfur hexafluoride and trifluoromethane. In a preferred embodiment, the compressed fluid is super critical carbon dioxide.

In all cases, the compressed fluid should be substantially miscible with the solvent while the compound to be precipitated should be substantially insoluble in the compressed fluid, i.e., the compound, at the selected solvent/compressed fluid contacting conditions, should be no more than about 5% by weight soluble in the compressed fluid, and preferably is essentially completely insoluble.

It is well within the level of those of skill in the art to determine the critical temperature and pressure for a given compressed fluid. In one embodiment, the compressed fluid is super critical carbon dioxide, and the critical temperature is at least 31.1° C. and up to about 60° C., and the critical pressure is at least 1071 psi and up to about 1800 psi. In another embodiment, the compressed fluid is super critical carbon dioxide, and the critical temperature is at least 31.1° C. and up to about 55° C., and the critical pressure is at least 1070 psi and up to about 1500 psi. It will be understood by those of skill in the art that the specific critical temperature and pressure may be different at different steps during the processing.

At block 208, the method 200 includes receiving the plurality of particles through the outlet of the pressurizable chamber. At block 210, the method 200 includes collecting the plurality of particles in a collection device. At block 212, the method 200 includes determining a size of one or more of the plurality of particles.

The flow rate can be adjusted as high as possible to optimize output but below the pressure limitations for the equipment, including the nozzle orifice. In another embodiment, a flow rate of the solution through the nozzle has a range from about 0.5 mL/min to about 30 mL/min. In various further embodiments, the flow rate is between about 0.5 mL/min to about 25 mL/min, 0.5 mL/min to about 20 mL/min, 0.5 mL/min to about 15 mL/min, 0.5 mL/min to about 10 mL/min, about 1 mL/min to about 30 mL/min, about 1 mL/min to about 25 mL/min, about 1 mL/min to about 20 mL/min, 1 mL/min to about 15 mL/min, about 1 mL/min to about 10 mL/min, about 2 mL/min to about 30 mL/min, about 2 mL/min to about 25 mL/min, about 2 mL/min to about 20 mL/min, about 2 mL/min to about 15 mL/min, or about 2 mL/min to about 10 mL/min.

The system may further include a particle size analyzer to determine a size and/or a size distribution (e.g., a mean, mode, or percentage of a size class) of particles created within the pressurizable chamber. In one example, the particle size analyzer may be an instrument configured to measure a size and/or a size distribution of particles created within the pressurizable chamber. Such a configuration may use dynamic light diffraction as the measuring technique. In another example, particle size and/or size distribution may be measured by particle counting. This technique tracks particles by the scattering of light off the particles. Such scattering may be tracked over a period of time and the path traveled and time is used to calculate the diffusion coefficient, which is then used to calculate the particle size and/or size distribution. Other particle size analyzers are possible as well.

In one embodiment, the method further includes the steps of determining a difference between a desired size of the one or more particles and the determined size of the one or more particles, and in response to the determined difference, adjusting at least one of the distance between the proximal end of the vessel and the outlet aperture of the nozzle and the angle between a longitudinal axis of the vessel and a longitudinal axis of the nozzle.

Further, the system described above may be a component of a larger particle production system. Such a particle production system may include one or more nozzle assemblies such as those described above, a sonic energy source positioned adjacent to the orifice of each nozzle, one or more particle filtration systems in communication with one or more nozzle assemblies, and one or more particle collection devices in communication with the one or more particle filtration systems. In one example, the one or more particle filtration systems comprise a tandem particle filtration system including at least one high pressure harvesting filter system and at least one low pressure collection filter system in tandem and downstream to the harvesting filter. In such an example, the particle production system may include at least two particle harvesting filters, two particle collection filters and two collection devices.

In another aspect, the invention provides compound particles prepared by the method of any embodiment or combination of embodiments of the invention.

EXAMPLES

Materials and Methods

Raw paclitaxel and docetaxel were purchased from Phyton Biotech (British Columbia, Canada), lot number FP2-15004 and DT7-14025, respectively. Both were characterized in their raw form. The milling of both drugs was accomplished using a Deco-PBM-V-0.41 mill (Deco). The milling conditions for both compounds were as follows:

Ball size=5 mm
RPM=600
Processing time=60 min
Room temperature.

Preparation of Paclitaxel Particles

A solution of 65 mg/ml of paclitaxel was prepared in acetone. A BETE MicroWhirl® fog nozzle (BETE Fog Nozzle, Inc) and a sonic probe (Qsonica, model number Q700) were positioned in the crystallization chamber approximately 8 mm apart. A stainless steel mesh filter with approximately 100 nm holes was attached to the crystallization chamber to collect the precipitated paclitaxel nanoparticles. The supercritical carbon dioxide was placed in the crystallization chamber of the manufacturing equipment and brought to approximately 1200 psi at about 38° C. and a flow rate of 24 kg/hour. The sonic probe was adjusted to 60% of total output power at a frequency of 20 kHz. The acetone solution containing the paclitaxel was pumped through the nozzle at a flow rate of 4.5 mL/minute for approximately 36 hours. Paclitaxel nanoparticles produced had an average number-weighted mean size of 0.81 μm with an average standard deviation of 0.74 μm over three separate runs.

Preparation of Docetaxel Particles

A solution of 79.32 mg/ml of docetaxel was prepared in ethanol. The nozzle and a sonic probe were positioned in the pressurizable chamber approximately 9 mm (apart. A stainless steel mesh filter with approximately 100 nm holes was attached to the pressurizable chamber to collect the precipitated docetaxel nanoparticles. The supercritical carbon dioxide was placed in the pressurizable chamber of the manufacturing equipment and brought to approximately 1200 psi at about 38° C. and a flow rate of 68 slpm. The sonic probe was adjusted to 60% of total output power at a frequency of 20 kHz. The ethanol solution containing the docetaxel was pumped through the nozzle at a flow rate of 2 mL/minute for approximately 95 minutes). The precipitated docetaxel agglomerates and particles were then collected from the supercritical carbon dioxide as the mixture is pumped through the stainless steel mesh filter. The filter containing the nanoparticles of docetaxel was opened and the resulting product was collected from the filter.

Docetaxel nanoparticles produced had an average number-weighted mean size of 0.82 μm with an average standard deviation of 0.66 μm over three separate ethanol runs.

Particle Size Analysis

Particle size was analyzed by both light obscuration and laser diffraction methods. An Particle Sizing Systems AccuSizer 780 SIS system was used for the light obscuration method and Shimadzu SALD-7101 was used for the laser diffraction method. Paclitaxel nanoparticles were analyzed using 0.10% (w/v) sodium dodecyl sulfate (SDS) in water as the dispersant. Docetaxel nanoparticles were analyzed using isopar G as the dispersant.

Paclitaxel suspensions were prepared by adding approximately 7 mL of filtered dispersant to a glass vial containing approximately 4 mg of paclitaxel particles. The vials were vortexed for approximately 10 seconds and then sonicated in a sonic bath approximately 1 minute. If the sample was already suspended, 1:1 solution of paclitaxel suspension to 0.1% SDS solution was made, vortexed for 10 seconds, and sonicated in the sonic bath for 1 minute.

Docetaxel suspensions were prepared by adding approximately 7 mL of filtered dispersant to a plastic vial containing approximately 4 mg of docetaxel particles. The vial was vortexed for approximately 10 seconds and then sonicated in a sonic bath for approximately 2 minutes. This suspension was used for laser diffraction analysis. Unused suspension was poured into a 125 mL particle-free plastic bottle, which was then filled to approximately 100 mL with filtered dispersant. The suspension was vortex for approximately 10 seconds and then sonicated in the sonic bath for approximately 2 minutes. This diluted suspension was used for light obscuration analysis.

A background test was first performed prior to analyzing particles on the AccuSizer 780 SIS. A new particle-free plastic bottle was filled with blank suspension solution by pumping from a reservoir, using a peristaltic pump, through a 0.22 µm Millipore filter and into the bottle. A background analysis was run to ensure the particle/mL count was below 100 particles/mL. A small amount of paclitaxel suspension, 5-100 µL, depending upon concentration of solution, was pipetted into the plastic bottle in place from the background test and was filled with ~100 mL dispersant and the analysis was started. Counts were monitored and paclitaxel solution added to reach and/or maintain 6000-8000 particle counts/mL during the entire analysis. Once the analysis was completed, the background data was removed and any measurement with less than four counts was removed.

To analyze particles on SALD-7101 using a batch cell, the analysis was started by choosing Manual Measurement. The refractive index was set as 1.5 to 1.7. The batch cell was filled with filtered dispersant just past the etched line. The blank measurement was ran. A small amount of API (paclitaxel or docetaxel) suspension was pipetted, generally <1 mL, depending upon concentration of solution as low as 100 µL, into the batch cell as needed to achieve an acceptable absorbance between 0.15 and 0.2 absorbance units. The measurements were executed, and the resulting graph with the highest level of confidence was selected; background was automatically accounted for.

BET Analysis

A known mass between 200 and 300 mg of the analyte was added to a 30 mL sample tube. The loaded tube was then mounted to a Porous Materials Inc. SORPTOMETER®, model BET-202A. The automated test was then carried out using the BETWIN® software package and the surface area of each sample was subsequently calculated.

Bulk Density Analyte

Paclitaxel or docetaxel particle preparations were added to a 10 mL tared graduated cylinder through a plastic weigh funnel at room temperature. The mass of the drug was measured to a nearest 0.1 mg, the volume was determined to the nearest 0.1 mL and the density calculated.

Dissolution Studies

Paclitaxel

Approximately 50 mg of material (i.e.: raw paclitaxel, milled paclitaxel, or paclitaxel particles) were coated on approximately 1.5 grams of 1 mm glass beads by tumbling the material and beads in a vial for approximately 1 hour. Beads were transferred to a stainless steel mesh container and placed in the dissolution bath containing methanol/water 50/50 (v/v) media at 37° C., pH 7, and a USP Apparatus II (Paddle), operating at 75 rpm. At 10, 20, 30, 60, and 90 minutes, a 5 mL aliquot was removed, filtered through a 0.22 µm filter and analyzed on a U(V/V) is spectrophotometer at 227 nm. Absorbance values of the samples were compared to those of standard solutions prepared in dissolution media to determine the amount of material dissolved.

Docetaxel

Approximately 50 mg of material (i.e.: raw docetaxel, milled docetaxel, or docetaxel particles) was placed directly in the dissolution bath containing methanol/water 15/85 (v/v) media at 37° C., pH 7, and a USP Apparatus II (Paddle), operating at 75 rpm. At 5, 15, 30, 60, 120 and 225 minutes, a 5 mL aliquot was removed, filtered through a 0.22 µm filter, and analyzed on a UV/VIS spectrophotometer at 232 nm. Absorbance values of the samples were compared to those of standard solutions prepared in dissolution media to determine the amount of material dissolved.

Results

The BET surface area of particles produced using the above protocol and variations thereof (i.e.: modifying nozzles, filters, sonic energy sources, flow rates, etc.) ranged between 22 and 39 $m^2/g$. FIG. 1 shows exemplary particles produced using the methods of the invention. By comparison, the BET surface area of raw paclitaxel was measured at 7.25 $m^2/g$ (FIG. 2), while paclitaxel particles made according to the methods of U.S. Pat. Nos. 5,833,891 and 5,874,029 ranged from 11.3 to 15.58 $m^2/g$. Exemplary particle sizes produced using the methods of the invention are shown in Table 1.

TABLE 1

| | Surface area | Mean Size µm | | St Dev µm | |
|---|---|---|---|---|---|
| | $m^2/g$ | Number | Volume | Number | Volume |
| 1 | 38.52 | 0.848 | 1.600 | 0.667 | 0.587 |
| 2 | 33.82 | 0.754 | 0.988 | 0.536 | 0.486 |
| 3 | 35.90 | 0.777 | 1.259 | 0.483 | 0.554 |
| 4 | 31.70 | 0.736 | 0.953 | 0.470 | 0.466 |
| 5 | 32.59 | 0.675 | 0.843 | 0.290 | 0.381 |
| 6 | 38.22 | 0.666 | 0.649 | 0.344 | 0.325 |
| 7 | 30.02 | 0.670 | 0.588 | 0.339 | 0.315 |
| 8 | 31.16 | 0.672 | 0.862 | 0.217 | 0.459 |
| 9 | 23.90 | 0.857 | 1.560 | 0.494 | 0.541 |
| 10 | 22.27 | 0.857 | 1.560 | 0.494 | 0.541 |
| 11 | 26.19 | 0.861 | 1.561 | 0.465 | 0.546 |

Comparative studies on bulk density, SSA, and dissolution rates (carried out as noted above) for raw drug, milled drug particles, and drug particles produced by the methods of the present invention are provided in Tables 2 and 3 below. The full dissolution time course for the paclitaxel and docetaxel materials are provided in Tables 4 and 5, respectively.

TABLE 2

Compound: Paclitaxel

| | | Particles | | | |
|---|---|---|---|---|---|
| Characteristic | Raw Material | Batch 1 | Batch 2 | Mean | Milled |
| Number Mean (um) | 1.16 | 0.83 | 0.67 | 0.75 | 0.89 |
| Volume Mean (um) | 1.29 | 1.42 | 0.57 | 1.00 | 1.35 |
| Bulk Density (g/cm$^3$) | 0.26 | 0.060 | 0.11 | 0.085 | 0.31 |
| Surface Area (m$^2$/g) | 10.4 | 35.6 | 39.8 | 37.7 | 15.0 |
| Dissolution (30 min) | 18% | 42% | 52% | 47% | 32% |

TABLE 3

Compound: Docetaxel

| | | Particles | | | |
|---|---|---|---|---|---|
| Characteristic | Raw Material | Batch 1 | Batch II | Mean | Milled |
| Number Mean (um) | 1.58 | 0.92 | 0.80 | 0.86 | 1.11 |

TABLE 3-continued

| Compound: Docetaxel | | | | | |
|---|---|---|---|---|---|
| | | Particles | | | |
| Characteristic | Raw Material | Batch 1 | Batch II | Mean | Milled |
| Volume Mean (um) | 5.05 | 4.88 | 4.03 | 4.46 | 3.73 |
| Bulk Density (g/cm3) | 0.24 | 0.062 | 0.096 | 0.079 | 0.44 |
| Surface Area (m2/g) | 15.9 | 43.0 | 45.4 | 44.2 | 15.2 |
| Dissolution (30 min) | 11% | 27% | 27% | 27% | 9% |

TABLE 4

| Paclitaxel Dissolution tune course | | | |
|---|---|---|---|
| Timepoint (minutes) | Paclitaxel Raw Material | Paclitaxel Particles | Milled Pactitaxel |
| 0 | 0.0% | 0.0% | 0.0% |
| 10 | 14.0% | 40.2% | 23.0% |
| 20 | 17.8% | 47.6% | 30.0% |
| 30 | 18.4% | 51.9% | 32.3% |
| 60 | 23.9% | 58.3% | 38.6% |
| 90 | 28.6% | 62.9% | 43.5% |

TABLE 5

| Docetaxel Dissolution time course | | | |
|---|---|---|---|
| Timepoint (minutes) | Docetaxel Raw Material | Docetaxel Particles | Milled Docetaxel |
| 0 | 0.0% | 0.0% | 0.0% |
| 5 | 3.2% | 12.1% | 3.2% |
| 15 | 6.9% | 21.7% | 5.9% |
| 30 | 11.2% | 27.2% | 9.3% |
| 60 | 16.4% | 32.9% | 12.2% |
| 120 | 22.4% | 38.9% | 13.6% |
| 225 | 26.8% | 43.1% | 16.0% |

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Since many modifications, variations, and changes in detail can be made to the described example, it is intended that all matters in the preceding description and shown in the accompanying figures be interpreted as illustrative and not in a limiting sense. Further, it is intended to be understood that the following clauses (and any combination of the clauses) further describe aspects of the present description.

We claim:

1. A nozzle assembly, comprising:

a vessel defining a pressurizable chamber, wherein the vessel includes a distal end and a proximal end;

an inlet of the pressurizable chamber at the proximal end of the vessel;

a nozzle positioned within the pressurizable chamber, wherein the nozzle includes an inlet tube in fluid communication with the inlet of the pressurizable chamber, wherein a longitudinal axis of the nozzle is aligned with a longitudinal axis of the inlet in a first position, wherein the nozzle includes an outlet aperture, wherein the nozzle is adjustable to alter a distance between the proximal end of the vessel and the outlet aperture of the nozzle, and wherein the nozzle is adjustable to alter an angle between the longitudinal axis of the inlet and the longitudinal axis of the nozzle from the first position to a second position;

a sonic energy source positioned distal to the outlet aperture of the nozzle, wherein the sonic energy source is adjustable to alter a distance between the outlet aperture of the nozzle and the sonic energy source and an angle between the sonic energy source and the longitudinal axis of the nozzle; and an outlet of the pressurizable chamber at the distal end of the vessel.

2. The nozzle assembly of claim 1, further comprising:

a second inlet of the pressurizable chamber at the proximal end of the vessel.

3. The nozzle assembly of claim 1, wherein the inlet of the pressurizable chamber is in fluid communication with a first reservoir and a second reservoir.

4. The nozzle assembly of claim 2, wherein the inlet of the pressurizable chamber is in fluid communication with a first reservoir, and wherein the second inlet of the pressurizable chamber is in fluid communication with a second reservoir.

5. The nozzle assembly of claim 1, wherein the outlet aperture of the nozzle includes a plurality of ridges to create a vortex within the nozzle.

6. The nozzle assembly of claim 1, wherein the inlet tube of the nozzle has an inner diameter with a range from about 1.5875 mm to about 6.35 mm.

7. The nozzle assembly of claim 1, further comprising:

a motor coupled to the nozzle, wherein the motor is configured to alter the distance between the proximal end of the vessel and the outlet aperture of the nozzle.

8. The nozzle assembly of claim 7, wherein the motor is further configured to alter the angle between a longitudinal axis of the vessel and a longitudinal axis of the nozzle.

9. A particle production system, comprising:

one or more nozzle assemblies of claim 1;

one or more particle filtration systems in communication with one or more nozzle assemblies; and one or more particle collection devices in communication with the one or more particle filtration systems.

10. The particle production system of claim 9, wherein the one or more particle filtration systems comprise a tandem particle filtration system including at least one high pressure harvesting filter system and at least one low pressure collection filter system in tandem and downstream to the harvesting filter.

11. The particle production system of claim 10, comprising at least two particle harvesting filters, two particle collection filters and two collection devices.

12. The particle production system of claim 9, wherein the one or more particle collection devices comprise:
- a collection vessel defining a chamber, wherein the collection vessel includes a distal end and a proximal end;
- an inlet port extending from the proximal end of the collection vessel, wherein the inlet port is in fluid communication with the chamber; and
- an outlet port extending from the proximal end of the collection vessel, wherein the inlet port is in fluid communication with the chamber, and wherein the outlet port includes a porous material positioned between the chamber and the outlet port.

13. The particle production system of claim 9, further comprising:
- a particle size analyzer configured to measure a size and/or a size distribution of one or more particles collected in the collection device.

14. A method comprising:
- providing a nozzle assembly including (i) a vessel defining a pressurizable chamber, wherein the vessel includes a distal end and a proximal end, (ii) a first inlet of the pressurizable chamber at the proximal end of the vessel, (iii) a nozzle positioned within the pressurizable chamber, wherein the nozzle includes an inlet tube in fluid communication with the inlet of the pressurizable chamber, wherein a longitudinal axis of the nozzle is aligned with a longitudinal axis of the inlet in a first position, wherein the nozzle includes an outlet aperture, wherein the nozzle is adjustable to alter a distance between the proximal end of the vessel and the outlet aperture of the nozzle, and wherein the nozzle is adjustable to alter an angle between the longitudinal axis of the inlet and the longitudinal axis of the nozzle from the first position to a second position, (iv) a sonic energy source positioned distal to the outlet aperture of the nozzle, wherein the sonic energy source is adjustable to alter a distance between the outlet aperture of the nozzle and the sonic energy source and an angle between the sonic energy source and the longitudinal axis of the nozzle, and (v) an outlet of the pressurizable chamber at the distal end of the vessel;
- receiving a first fluid and a second fluid into the pressurizable chamber, wherein the first fluid is transported through the outlet aperture of the nozzle and onto the sonic energy source, and wherein the second fluid is transported through a second inlet of the pressurizable chamber to thereby create a plurality of particles within the pressurizable chamber;
- receiving the plurality of particles through the outlet of the pressurizable chamber;
- collecting the plurality of particles in a collection device; and
- determining a size of one or more of the plurality of particles.

15. The method of claim 14, further comprising:
- determining a difference between a desired size of the one or more particles and the determined size of the one or more particles.

16. The method of claim 15, further comprising:
- in response to the determined difference, adjusting at least one of the distance between the proximal end of the vessel and the outlet aperture of the nozzle and the angle between a longitudinal axis of the vessel and a longitudinal axis of the nozzle.

17. The method of claim 14, wherein a flow rate of the first fluid through the nozzle has a range from about 0.5 mL/min to about 30 mL/min.

18. The method of claim 14, wherein the plurality of particles formed within the pressurizable chamber contain high pressure fluid suspension.

19. The method of claim 14, wherein the sonic energy source produces sonic energy with an amplitude between about 10% and about 100% of the maximum sonic energy output of the sonic energy source.

20. A non-transitory computer readable medium having stored thereon instructions, that when executed by one or more processors, causes the particle production system of claim 9 to perform operations comprising:
- receiving a first fluid and a second fluid into the pressurizable chamber, wherein the first fluid is transported through the outlet aperture of the nozzle and onto the sonic energy source, and wherein the second fluid is transported through a second inlet of the pressurizable chamber to thereby create a plurality of particles within the pressurizable chamber;
- receiving the plurality of particles through the outlet of the pressurizable chamber;
- collecting the plurality of particles in a collection device; and
- determining a size of one or more of the plurality of particles.

21. The non-transitory computer readable medium of claim 20, wherein the operations further comprise:
- determining a difference between a desired size of the one or more particles and the determined size of the one or more particles.

22. The non-transitory computer readable medium of claim 21, wherein the operations further comprise:
- in response to the determined difference, adjusting at least one of the distance between the proximal end of the vessel and the outlet aperture of the nozzle and the angle between a longitudinal axis of the vessel and a longitudinal axis of the nozzle.

* * * * *